United States Patent [19]

Rubin et al.

[11] Patent Number: 5,612,194
[45] Date of Patent: Mar. 18, 1997

[54] METHODS OF PRODUCING EFFECTIVE RECOMBINANT SERINE PROTEASE INHIBITORS AND USES OF THESE INHIBITORS

[75] Inventors: Harvey Rubin, Philadelphia; Barry Cooperman, Penn Valley; Norman Schechter, Philadelphia; Michael Plotnick, Havertown; Zhi M. Wang, Philadelphia, all of Pa.

[73] Assignee: Trustees of the University of Pennsylvania, Philadelphia, Pa.

[21] Appl. No.: 276,936

[22] Filed: Jul. 19, 1994

Related U.S. Application Data

[63] Continuation-in-part of Ser. No. 229,286, Apr. 18, 1994, abandoned, which is a continuation-in-part of Ser. No. 221,078, Mar. 31, 1994, and Ser. No. 221,171, Mar. 31, 1994, said Ser. No. 221,078, and Ser. No. 221,171, each is a continuation-in-part of Ser. No.5,898, Jan. 15, 1993, abandoned, and Ser. No. 5,908, Jan. 15, 1993, Pat. No. 5,367,064, each is a division of Ser. No.735,335, Jul. 24, 1991, Pat. No. 5,252,725, which is a division of Ser. No. 370,704, Jun. 23, 1989, Pat. No. 5,079,336.

[51] Int. Cl.$^6$ .......................... A61K 38/55; A61K 38/57; C07K 14/81; C12N 15/15
[52] U.S. Cl. ........................ 435/69.2; 435/172.3; 514/12; 530/350
[58] Field of Search ................................ 435/172.3, 69.2, 435/212, 218, 213; 514/2, 12; 530/350, 395

[56] References Cited

PUBLICATIONS

Austin, R.C., et al. *FEBS Letters* 280(2):254–258 (1991).
Hopkins, P.C.R., et al. *Biochemistry* 32:7650–7657 (1993).
Davis, A.E. et al. *Nature Genetics* 1:354–358 (1992).
Baird et al., "$O_2$ Metabolites and Neutrophil Elastase Synergistically Cause Edematous Injury In Isolated Rat Lungs," *J. Appl. Physiol.* 1986, 61, 2224–2229.
Cooperman et al., "Antichymotrypsin Interaction with Chymotrypsin," *J. Biol. Chem.* 1993, 268, 23616–23625.
Emerson et al., "Protection Against Disseminated Intravascular Coagulation and Death by Antithrombin–III in the *Escherichia coli* Endotoxemic Rat," *Circ. Shock* 1987, 21, 1–13.
Eriksson et al., "Familial $\alpha_1$–Antichymotrypsin Deficiency," *Acta. Med. Scand.* 1986, 220, 447–453.
Gennaro, Alfonso, ed., *Remington's Pharmaceutical Sciences*, 18th ed., 1990, Mack Pub. Co., Easton, PA.
Jiang et al., "Mutually Exclusive Exon Use and Reactive Center Diversity in Insect Serpins", *J. Biol. Chem.* 1994, 269, 55–58.
Nagai et al., "Administration of $\alpha_1$–Proteinase Inhibitor Ameliorates Bleomycin–induced Pulmonary Fibrosis in Hamsters $^{1-4}$," *Am. Rev. Resp. Dis.* 1992, 145, 651–656.
Poller et al., "A Leucine–to–Proline Substitution Causes a Defective $\alpha_1$–Antichymotrypsin Allele Associated with Familial Obstructive Lung Disease," *Genomics* 1993, 17, 740–743.
Redens et al., "Synergistic Protection from Lung Damage by Combining Antithrombin–III and Alpha$_1$–Proteinase Inhibitor in the *E. coli* Endotoxemic Sheep Pulmonary Dysfunction Model," *Circ. Shock* 1988, 26, 15–26.
Rosengren et al., "Neutrophil–mediated Vascular Leakage is Not Supressed by Leukocyte Elastase Inhibitors," *Am. J. Physiol.* 1990, 259, H1288–H1294.
Schechter et al., "On Size of the Active Site in Proteases. I. Papain," *Biochem. and Biophys. Res. Com.* 1967, 27, 157–162.
Schechter et al., "Reaction of Human Chymase with Reactive Site Variants of $\alpha$1–Antichymotrypsin," *J. Biol. Chem.* 1993, 268, 23626–23633.

*Primary Examiner*—Dian C. Jacobson
*Attorney, Agent, or Firm*—Law Offices of Jane Massey Licata

[57] ABSTRACT

A method of producing a recombinant serine protease inhibitor capable of effectively modulating serine protease activity is provided. Compositions capable of modulating serine protease activity and use of such compositions to regulate inflammatory processes in cells are also provided.

5 Claims, No Drawings

SEQUENCE LISTING ( 1 ) GENERAL INFORMATION:

( i i i ) NUMBER OF SEQUENCES: 30

( 2 ) INFORMATION FOR SEQ ID NO: 1:

( i ) SEQUENCE CHARACTERISTICS:
        ( A ) LENGTH: 4
        ( B ) TYPE: Amino Acid
        ( D ) TOPOLOGY: Linear ( x i ) SEQUENCE DESCRIPTION: SEQ ID NO: 1:

```
Ala  Ala  Pro  Val
1
```

( 2 ) INFORMATION FOR SEQ ID NO: 2:

( i ) SEQUENCE CHARACTERISTICS:
        ( A ) LENGTH: 4
        ( B ) TYPE: Amino Acid
        ( D ) TOPOLOGY: Linear ( x i ) SEQUENCE DESCRIPTION: SEQ ID NO: 2:

```
Ala  Ala  Pro  Phe
1
```

( 2 ) INFORMATION FOR SEQ ID NO: 3:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 3:

```
Thr  Glu  Ala  Ser  Ala  Ala  Thr  Ala  Val  Lys  Ile  Thr  Leu  Leu  Ser
1                  5                        10                       15
Ala  Leu  Val  Glu  Thr  Arg  Thr  Ile  Val  Arg  Phe  Asn
                   20                        25
```

( 2 ) INFORMATION FOR SEQ ID NO: 4:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 4:

```
Thr  Glu  Ala  Ser  Ala  Ala  Thr  Ala  Val  Lys  Ile  Thr  Leu  Met  Ser
1                  5                        10                       15
Ala  Leu  Val  Glu  Thr  Arg  Thr  Ile  Val  Arg  Phe  Asn
                   20                        25
```

( 2 ) INFORMATION FOR SEQ ID NO: 5:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 5:

```
Thr  Glu  Ala  Ser  Ala  Ala  Thr  Ala  Val  Lys  Ile  Thr  Leu  Arg  Ser
1                  5                        10                       15
Ala  Leu  Val  Glu  Thr  Arg  Thr  Ile  Val  Arg  Phe  Asn
                   20                        25
```

( 2 ) INFORMATION FOR SEQ ID NO: 6:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 6:

```
Thr Glu Ala Ser Ala Ala Thr Ala Val Lys Ile Thr Leu Trp Ser
 1               5                   10                  15
Ala Leu Val Glu Thr Arg Thr Ile Val Arg Phe Asn
                20                  25
```

( 2 ) INFORMATION FOR SEQ ID NO: 7:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 7:

```
Thr Glu Ala Ser Ala Ala Thr Ala Val Lys Ile Thr Leu Leu Ser
 1               5                   10                  15
Ala Val Val Glu Thr Arg Thr Ile Val Arg Phe Asn
                20                  25
```

( 2 ) INFORMATION FOR SEQ ID NO: 8:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 8:

```
Thr Glu Ala Ser Ala Ala Thr Ala Val Lys Ile Ile Pro Met Ser
 1               5                   10                  15
Ile Pro Val Glu Thr Arg Thr Ile Val Arg Phe Asn
                20                  25
```

( 2 ) INFORMATION FOR SEQ ID NO: 9:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 9:

```
Thr Glu Ala Ser Ala Ala Thr Ala Leu Glu Ala Ile Pro Met Ser
 1               5                   10                  15
Ile Pro Val Glu Thr Arg Thr Ile Val Arg Phe Asn
                20                  25
```

( 2 ) INFORMATION FOR SEQ ID NO: 10:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 10:

```
Thr Glu Ala Ser Gly Thr Thr Ala Val Lys Ile Thr Leu Leu Ser
 1               5                   10                  15
Ala Leu Val Glu Thr Arg Thr Ile Thr Arg Phe Asn
                20                  25
```

( 2 ) INFORMATION FOR SEQ ID NO: 11:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 11:

```
Thr Glu Ala Ser Gly Thr Thr Ala Val Lys Ile Thr Leu Phe Ser
1               5                   10                  15
Ala Leu Val Glu Thr Arg Thr Ile Thr Arg Phe Asn
                20                  25
```

( 2 ) INFORMATION FOR SEQ ID NO: 12:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 12:

```
Thr Glu Ala Ser Gly Thr Thr Ala Val Lys Ile Thr Leu Met Ser
1               5                   10                  15
Ala Leu Val Glu Thr Arg Thr Ile Thr Arg Phe Asn
                20                  25
```

( 2 ) INFORMATION FOR SEQ ID NO: 13:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 13:

```
Thr Glu Ala Ser Gly Thr Thr Ala Val Lys Ile Ile Pro Met Ser
1               5                   10                  15
Ile Pro Val Glu Thr Arg Thr Ile Thr Arg Phe Asn
                20                  25
```

( 2 ) INFORMATION FOR SEQ ID NO: 14:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 14:

```
Thr Glu Ala Ser Gly Thr Thr Ala Val Lys Ile Ile Pro Leu Ser
1               5                   10                  15
Ile Pro Val Glu Thr Arg Thr Ile Thr Arg Phe Asn
                20                  25
```

( 2 ) INFORMATION FOR SEQ ID NO: 15:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 15:

```
Thr Glu Ala Ser Gly Thr Thr Ala Val Lys Val Ile Ser Ala Glu
1               5                   10                  15
Trp Met Val Glu Thr Arg Thr Ile Thr Arg Phe Asn
                20                  25
```

( 2 ) INFORMATION FOR SEQ ID NO: 16:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 16:

```
Thr Glu Ala Ser Gly Thr Met Phe Leu Glu Ala Ile Pro Met Ser
1               5                   10                  15
Ile Pro Pro Glu Thr Arg Thr Ile Thr Arg Phe Asn
                20                  25
```

( 2 ) INFORMATION FOR SEQ ID NO: 17:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 17:

```
Thr Glu Ala Ser Gly Thr Met Phe Leu Glu Ala Ile Pro Met Ser
1               5                   10                  15
Ile Pro Pro Glu Thr Arg Thr Ile Ala Arg Phe Asn
                20                  25
```

( 2 ) INFORMATION FOR SEQ ID NO: 18:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 18:

```
Thr Glu Ala Ser Gly Thr Met Phe Leu Glu Ala Ile Pro Met Ser
1               5                   10                  15
Ile Pro Pro Glu Val Lys Phe Asn Thr Arg Phe Asn
                20                  25
```

( 2 ) INFORMATION FOR SEQ ID NO: 19:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 19:

```
Arg Glu Ala Ser Ala Ala Thr Ala Val Lys Ile Thr Leu Leu Ser
1               5                   10                  15
Ala Leu Val Glu Thr Arg Thr Ile Val Arg Phe Asn
                20                  25
```

( 2 ) INFORMATION FOR SEQ ID NO: 20:

( i ) SEQUENCE CHARACTERISTICS:
        ( A ) LENGTH: 27
        ( B ) TYPE: Amino Acid
        ( D ) TOPOLOGY: Linear ( x i ) SEQUENCE DESCRIPTION: SEQ ID NO: 20:

```
Thr Glu Arg Ser Ala Ala Thr Ala Val Lys Ile Thr Leu Leu Ser
1               5                   10                  15
Ala Leu Val Glu Thr Arg Thr Ile Val Arg Phe Asn
                20                  25
```

(2) INFORMATION FOR SEQ ID NO: 21:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 21:

```
Thr Glu Ala Ser Ala Arg Thr Ala Val Lys Ile Thr Leu Leu Ser
1               5                   10                  15
Ala Leu Val Glu Thr Arg Thr Ile Val Arg Phe Asn
                20                  25
```

(2) INFORMATION FOR SEQ ID NO: 22:

(i) SEQUENCE CHARACTERISTICS:
        (A) LENGTH: 23
        (B) TYPE: Amino Acid
        (D) TOPOLOGY: Linear (xi) SEQUENCE DESCRIPTION: SEQ ID NO: 22:

```
Thr Glu Ala Ser Gly Thr Thr Ala Val Lys Ile Ile Pro Met Ser
1               5                   10                  15
Ile Pro Pro Glu Thr Arg Phe Asn
                20
```

(2) INFORMATION FOR SEQ ID NO: 23:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 23:

```
Thr Glu Ala Ser Ala Ala Thr Ala Val Lys Ile Ile Pro Arg Ser
1               5                   10                  15
Ile Pro Val Glu Thr Arg Thr Ile Val Arg Phe Asn
                20                  25
```

(2) INFORMATION FOR SEQ ID NO: 24:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 24:

```
Thr Glu Ala Ser Ala Ala Thr Ala Val Lys Ile Met Pro Leu Ser
1               5                   10                  15
Thr Gln Val Glu Thr Arg Thr Ile Val Arg Phe Asn
                20                  25
```

(2) INFORMATION FOR SEQ ID NO: 25:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 25:

```
Thr Glu Ala Ser Ala Ala Thr Ala Val Lys Ile Ala Gly Arg Ser
1               5                   10                  15
Leu Asn Val Glu Thr Arg Thr Ile Val Arg Phe Asn
                20                  25
```

(2) INFORMATION FOR SEQ ID NO: 26:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 26:

```
Thr Glu Ala Ser Ala Ala Thr Ala Val Lys Ile Val Ala Arg Thr
1               5                   10                  15

Leu Leu Val Glu Thr Arg Thr Ile Val Arg Phe Asn
                20                  25
```

(2) INFORMATION FOR SEQ ID NO: 27:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 27:

```
Thr Glu Ala Ser Ala Ala Thr Ala Val Lys Ile Ser Ala Arg Met
1               5                   10                  15

Ala Pro Val Glu Thr Arg Thr Ile Val Arg Phe Asn
                20                  25
```

(2) INFORMATION FOR SEQ ID NO: 28:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 28:

```
Thr Glu Ala Ser Ala Ala Thr Ala Val Lys Ile Met Ser Arg Met
1               5                   10                  15

Ser Leu Val Glu Thr Arg Thr Ile Val Arg Phe Asn
                20                  25
```

(2) INFORMATION FOR SEQ ID NO: 29:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 29:

```
Thr Glu Ala Ser Ala Ala Thr Ala Val Lys Ile Thr Phe Arg Ser
1               5                   10                  15

Ala Arg Val Glu Thr Arg Thr Ile Val Arg Phe Asn
                20                  25
```

(2) INFORMATION FOR SEQ ID NO: 30:

(i) SEQUENCE CHARACTERISTICS:
        (A) LENGTH: 27
        (B) TYPE: Amino Acid
        (D) TOPOLOGY: Linear (xi) SEQUENCE DESCRIPTION: SEQ ID NO: 30:

```
Thr Glu Ala Ala Gly Ala Met Phe Leu Glu Ala Ile Pro Met Ser
1               5                   10                  15
```

| Ile | Pro | Pro | Glu | Val | Lys | Phe | Asn | Lys | Pro | Phe | Thr |
|---|---|---|---|---|---|---|---|---|---|---|---|
| | | | | 20 | | | | 25 | | | |

METHODS OF PRODUCING EFFECTIVE RECOMBINANT SERINE PROTEASE INHIBITORS AND USES OF THESE INHIBITORS

This application is a continuation-in-part application of U.S. application Ser. No. 08/229,286, filed Apr. 18, 1994, now abandoned, which is a continuation-in-part of U.S. application Ser. No. 08/221,078, filed Mar. 31, 1994, and U.S. application Ser. No. 08/221,171, filed Mar. 31, 1994, each of which is a continuation-in-part of application Ser. No. 005,898, filed Jan. 15, 1993, now abandoned, and application Ser. No. 08/005,908, filed Jan. 15, 1993, now U.S. Pat. No. 5,367,064, both of which are divisionals of application Ser. No. 07/735,335, filed Jul. 24, 1991, now U.S. Pat. No. 5,252,725, which is a divisional of application Ser. No. 07/370,704, filed Jun. 23, 1989, now U.S. Pat. No. 5,079,336.

BACKGROUND OF THE INVENTION

Serine protease inhibitors or "serpins" are a superfamily of inhibitors involved in the mediation of a variety of biological processes essential to survival of a host. Members of the serpin family play a role in a great number of biological processes including, but not limited to, inflammation, fertilization, tumor migration, neurotropism, and heat shock. Maspin was recently identified and characterized as a protective serpin normally present in mammary epithelium but absent from most mammary carcinoma cell lines. Serpins are found in plants, prokaryotes, insects and animals. Natural mutations and modifications of serpins are correlated with a number of serious disease states. Serpin dysfunction is associated with lung, liver and blood coagulation diseases such as emphysema, liver cirrhosis, thrombosis and pulmonary embolism.

The interaction of serpins with endogenous and microbial proteases produces a spectrum of molecular species, each of which are components of a highly evolutionarily conserved homeostatic mechanism that operates to maintain concentrations of intact, active serpins essential to a host's survival. For example, the serpin-protease complex and the hydrolyzed, inactive form of the intact serpin stimulate the production of interleukin-6, signaling hepatocytes to increase synthesis of the acute phase proteins including a subpopulation of the serpin superfamily of proteins. While serpin-enzyme complexes are rapidly cleared from the circulation, cleaved and intact forms of these complexes can accumulate in local areas of inflammation. This accumulation establishes a complex microenvironment of chemoattractants and inhibitors of chemotaxis as well as activators and inhibitors of neutrophil degranulation, leukotrienes, platelet activating factor (PAF), and superoxide production. The extreme virulence of several pox viruses has been attributed in part to a serpin whose target is cysteine proteinase ICE, the interleukin 1-β converting enzyme.

Through various animal models, it has been demonstrated that uncontrolled serine protease activity is a major mechanism of lung injury and that an appropriate serpin response controls the degree of the injury. For example, antithrombin III (ATIII) in combination with α-1-protease inhibitor (α1P1), protected sheep from endotoxin-induced lung injury where the individual serpins were not as effective as the combination. Redens et al., *Circ. Shock* 1988, 26, 15. Redens et al. also showed that ATIII protects against the development of disseminated intravascular coagulation in endotoxemic rats. Emerson et al., *Circ. Shock* 1987, 21, 1. A scavenger of $H_2O_2$ and a chloromethyl ketone inhibitor of elastase blocked reactive oxygen potentiation of neutrophil elastase-mediated acute edematous lung injury in a rat and α1P1 diminished bleomycin-mediated pulmonary inflammation as well as subsequent fibrosis. Baird et al., *Physiol.* 1986, 61, 2224 and Nagai et al., *Am. Rev. Resp. Dis.* 1992, 145, 651. In another system, however, neutrophil elastase inhibitors, Eglin C and a low molecular weight compound L 658,758, failed to inhibit leukotriene B4-induced-neutrophil-mediated adherence, diapedesis or vascular leakage. Rosengren et al., *Am J. Physiol.* 1990, 259, H1288. As shown by these studies, inhibitors of proteolytic enzymes administered therapeutically can limit the molecular and cellular mechanism of inflammation and reduce tissue damage.

There are two subfamilies within the serpin superfamily. One family contains proteins for which no cognate serine proteases have yet been identified. Examples of proteins in this subfamily include ovalbumin, angiotensinogen and steroid binding globulins. The second family contains members for which at least one serine protease can be found as an inhibitory target. The subfamily of serpins that inhibit serine proteases have characteristic properties that define the activity of the inhibitor, i.e., second order rate constants for inhibition of their cognate enzyme range between $10^2$ and $10^7$ $M^{-1}s^{-1}$; the enzyme-inhibitor complex is stable under certain conditions and can be detected as a species with a molecular weight greater than the individual components in SDS polyacrylamide gels; and, a large conformational change occurs upon cleavage of the sessile bond in the reactive center leading to increased thermal stability of the protein. An example of a serpin in this subfamily is α1-antichymotrypsin (ACT), an inhibitor of chymotrypsin (Chtr). ACT is synthesized predominantly by the liver and is one of the acute phase reactants with levels rising rapidly to more than 5 fold in response to a wide variety of injuries including surgery, acute myocardial infarctions, burns, autoimmune diseases, malignancies, infections and liver allograft rejection. ACT has also been linked with the plasticity of the nervous system and associated with beta amyloid deposits in Alzheimer's disease, in aging brain, Down's syndrome and in the Dutch variant of hereditary cerebral hemorrhage with amyloidosis. It has been demonstrated that both native ACT and recombinant ACT (rACT) inhibit superoxide generation by human neutrophils in suspension.

In general, the reactive loop of an inhibitory serpin is comprised of a relatively short amino acid sequence. The selectivity of setpins for inhibiting a specific type of protease depends on the amino acid sequence of a reactive center region exposed on the surface of the serpin. Jiang H. et al., *J. Biol. Chem.* 1994, 269, 55–58, demonstrated that the selectivity of serpins from a lepidopteran insect, *Manduca sexta*, can be altered by changing the amino acid sequence in the reactive loop. It was found that pre-mRNA splicing generates inhibitor diversity and the potential to regulate a variety of proteinases, using the same protein framework joined to different reactive site region cassettes.

Based upon three dimensional structures of complexes formed by small inhibitors (about 50 amino acids) with their target enzymes, it is believed that the P3-P3' region, amino acids 356–361 in ACT, (nomenclature of Schecter I. and Berger A.C. *Biochemistry Biophysics Research Communication* 1967, 27:157), in the loop of serpins, or so-called "active site region" (or bait region) serves as a primary contact site or binding site with the protease. It has now been found that another part of the loop (from P14 to P9), denoted the "hinge region", is also important for the inhibitory activities of serpins. A method has now been developed for modulating serine protease activity in cells or tissues which comprises selecting a target protease which accumulates in cells or tissues, producing a recombinant serine protease inhibitor having a protease binding site and a hinge region of a reactive center loop which have modified amino acid sequences so that interaction between the inhibitor and the target protease is altered, and contacting cells or tissues with the modified serine protease inhibitor so that serine protease activity is modulated. Compositions capable of effectively modulating serine protease activity which comprise a recombinant serine protease inhibitor having a protease binding site and a hinge region of a reactive loop which have modified amino acid sequences are also provided. These compositions are useful in regulating inflammatory processes. In addition, a method is provided for producing serine protease inhibitors capable of effectively modulating the activity of the serine proteases which comprises determining a sequence of a serine protease inhibitor; identifying a reactive loop of said serine protease inhibitor, said reactive loop containing a first amino acid sequence of a protease binding site and a second amino acid sequence of a hinge region; modifying the first amino acid sequence of said protease binding site so that the selectivity of a recombinant serine protease inhibitor for other proteases is altered; modifying the second amino acid sequence of said hinge region so that said recombinant serine protease inhibitor is capable of effectively modulating the activity of the serine protease; and synthesizing this modified serine protease inhibitor.

SUMMARY OF THE INVENTION

An object of the present invention is to provide a method of producing a recombinant serine protease inhibitor capable of effectively modulating serine protease activity which comprises determining a sequence of a selected serine protease inhibitor; identifying a reactive loop of said serine protease inhibitor, said reactive loop containing a first amino acid sequence of a protease binding site and a second amino acid sequence of a hinge region; modifying the first amino acid sequence of said protease binding site so that the selectivity of a recombinant serine protease inhibitor for other proteases will be altered; modifying the second amino acid sequence of said hinge region so that said recombinant serine protease inhibitor will effectively modulate an activity of the protease; and synthesizing the modified recombinant serine protease inhibitor.

Another object of the present invention is to provide a composition capable of effectively modulating serine protease activity which comprises a recombinant serine protease inhibitor having a protease binding site and a hinge region of a reactive loop which have modified amino acid sequences.

Yet another object of the present invention is to provide a method of modulating a serine protease activity in cells or tissues which comprises selecting a target protease which accumulates in cells or tissues; producing a recombinant serine protease inhibitor having a protease binding site and a hinge region of a reactive center loop which have modified amino acid sequences so that interaction between the inhibitor and the target protease is altered; and contacting cells or tissues with the modified serine protease inhibitor so that serine protease activity is modulated.

DETAILED DESCRIPTION OF THE INVENTION

Serine protease inhibitors of the serpin superfamily of glycoproteins are important in maintaining homeostasis in the body. Serpins regulate proteases involved in a range of important biological processes including, but not limited to, blood coagulation, fertilization and inflammation. The various serpins in animals and insects are believed to have evolved through gene duplication and divergence, resulting in a large number of serpin genes within a single organism, each encoding a protein with a unique reactive site region and physiological function. An example of a serpin is antichymotrypsin (ACT) which inhibits chymotrypsin, pancreatic elastase, mast cell chymase and cathepsin G. Elevated levels of ACT have been observed in a wide variety of injuries including surgery, acute myocardial infarctions, burns, autoimmune diseases, malignancies, infections and liver allograft rejection.

ACT has been associated with certain cell mediated and cytokine mediated events. For example, tumor necrosis factor enhances platelet activation through TNF-mediated release of cathepsin G from neutrophils. This effect can be blocked by ACT. In addition, the synthesis and release of leukotriene B4 and platelet activating factor from TNF-stimulated neutrophils can be blocked by ACT. Neutrophil cathepsin G and mast cell chymase are major components in the inflammatory response in skin and in the lung. Therefore, it has been suggested that ACT plays a regulatory role in limiting inflammation that arises secondary to the release of the enzymatic contents of the granules. Native and recombinant ACT have also been shown to inhibit superoxide generation by human neutrophils. In the intact cell system, both intact ACT and ACT complexed with chymotrypsin were foundequally effective in inhibiting free radical production by human neutrophils stimulated with either f-Met-Leu-Phe, Con A or PMA. Families with only 50% of normal circulating ACT have been found to have abnormalities in lung function with large residual volumes and an increase in atopic diseases. Thus, it appears that intact ACT, as well as cleaved and complexed forms of ACT, play a central role in regulating inflammation and certain developmental events.

ACT shares a number of properties with other members in the serpin family. The most important feature of ACT and other serpins which retain inhibitory activity and specificity is the presence of a mobile reactive loop.

Serine protease inhibitors or "serpins" are believed to inhibit their target serine proteases in accordance with the following general mechanism. The serine protease requires the serpin as a substrate, and initiates proteolytic attack. Serpins form tight 1:1 complexes with their target proteases through an interaction with a specific site, the P1 residue. The standard notation denotes the P1 position as the position immediately N terminal to the cleavage site, P2 is N terminal to P1, and so forth. The P1 position is located in an exposed region of the serpin referred to as the reactive loop. There is a large body of structural data derived from peptide inhibitors demonstrating that the reactive loop of the inhibitor is in an antiparallel beta strand conformation, referred to as "canonical". However, it has now been found that the reactive loop of an intact serpin assumes a somewhat distorted helical conformation with the P1 side chain extending outwardly from the rest of the serpin. The reactive loop is not preorganized in a canonical, antiparallel beta strand conformation, but rather there appears to be subsequent helix destabilization for productive binding with the protease. Binding to the protease induces a conformational change in the serpin, which under certain conditions, propagates to alter the conformation of the protease itself. The altered conformation of the protease effectively eliminates its enzymatic activity, and thus the enzymatic reaction pathway of the protease is arrested.

An important focus of serpin research has been the relationship between an imbalance between serpins and their target enzymes and tissue destruction and degenerative diseases. Through a detailed investigation of the biochemical and structural properties of the interaction of serpins, and genetically engineered variants of serpins, with target proteases, a rational design of new proteins having therapeutic activity has now been developed. According to a 3-dimensional model of complexes formed by small peptide inhibitors (about 50 amino acids) with their target enzymes, it is believed that the P3–P3' region in the loop of serpins, also referred to as the "active site region" or the "bait region" serves as the primary contact site or binding site with the enzyme. The inhibitory activity of a serpin for a selected enzyme can be altered by modifying amino acids, either by mutation or deletion, in this protease binding site region. For example, it was found that substituting a leucine with a methionine at the P1' position of wild type ACT resulted in a mutant with the ability to partially inhibit human neutrophil elastase, while maintaining its ability to inhibit chymotrypsin, cathepsin-G and chymase (See Tables 1 and 2). It was also found that a variant in which the P6'–P9' residues of the reactive loop were deleted retained serine protease inhibitory activity against chymotrypsin and enhanced the activity against human neutrophil elastase. The activities of human neutrophil elastase, chymotrypsin, cathepsin G and chymase were measured in accordance with methods described in Examples 2 through 5 of this application. Plasmin and thrombin activities were also measured in accordance with methods well known in the art, for example Cooperman et al., *J. Biol. Chem.* 1993, 268, 23616.

It has also been found that the hinge region (P14–P9) is an important component of the loop for maintaining the inhibitory activity of serpins. Amino acid sequence alignment has shown that the hinge region of each inhibitory serpin is strongly conserved for amino acids with small and neutral side chains, such as alanines or threonines, as opposed to charged residues such as arginine and glutamic acid. The replacement of threonine at P14 with arginine in a recombinant ACT (rACT) leads to a substrate which has lost its inhibitory activity (See Tables 1 and 2).

In the present invention, a method is provided for producing a recombinant serine protease inhibitor capable of effectively modulating their activities. In this method, a sequence of a selected serine protease inhibitor is determined and the reactive loop of the serine protease inhibitor is identified. The amino acid sequence of the protease binding site of this loop is then modified to alter the selectivity of the serine protease inhibitor for various other proteases. Modifications to the protease binding site can comprise substitution or deletion of one or more amino acids in the sequence. In a preferred embodiment, the modification will consist of substituting a few amino acids in the protease binding site region with amino acids known to be in other serine protease inhibitors. For example, the substitution of the leucine at the P1' position of ACT with a methionine (which is the amino acid present at this position in the serpin α1P1, an inhibitor of human neutrophil elastase) results in a mutant with the ability to inhibit chymotrypsin, cathepsin-G, chymase and human neutrophil elastase (see Tables 1 and 2). appropriate substitutions in the amino acid sequence of the protease binding site can be routinely determined by one of skill in the art in accordance with the teachings of the present invention. The amino acid sequence of the hinge region can also be modified. In a preferred embodiment, the hinge region is modified to contain primarily amino acids having small, neutral chains, such as alanines or threonines. This modified recombinant serine protease inhibitor is then synthesized. Modifications can be performed using standard site-directed mutagenesis techniques well known to those of skill in the art.

In one embodiment of the present invention, the method is used to produce analogues of ACT. ACT appears to be unique among serpins in its ability to bind DNA. ACT has been localized in the nuclei of certain malignant and nonmalignant cells and has been reported to inhibit DNA polymerase alpha, DNA synthesis in permeabilized human carcinoma cells, and poly-C-dependent primase, and to stimulate poly dT dependent primase. It has now been found that lysine residues within two short regions of rACT are important for DNA binding. rACT has two elements, a stretch of lysines (residues 210–212) and the C terminal peptide 390–398, containing two lysines which are involved in DNA binding interaction. Replacement of the lysines 210–212 by glutamates or threonines resulted in the complete loss of DNA binding activity. Partial DNA binding activity was retained upon replacement of only one or two of the lysines with threonine. With respect to the C-terminal peptide, it was found that acetylation of K396, the most reactive lysine in rACT, was diminished in the presence of DNA, and replacement of the two lysines, K391 and K396, with threonine resulted in a protein with very little DNA binding capability. Therefore, when producing and selecting recombinant ACT analogues, further modifications can be made at lysines 210–212 and in the C terminal peptide, 390–398 so that DNA binding of the inhibitor is modulated.

Studies on the interactions between serpins and serine proteases have shown that the conformational change accompanying binding of the serpin to the protease is important in the inhibition of a selected serlne protease activity.

In accordance with the teachings of the present invention compositions are also provided which are capable of effectively modulating serine protease activity. A composition of the present invention comprises a recombinant serine protease inhibitor having a protease binding site and a hinge region of a reactive loop which have modified amino acid sequences. In a preferred embodiment the modified amino acid sequence of the hinge region comprises amino acids with small and neutral side chains such as alanines and threonines. Compositions of the present invention are especially useful in regulating inflammatory processes related to serine proteases accumulating in cells or tissues.

A method of modulating a serine protease activity in cells or tissues is also provided in the present invention. This method comprises selecting a target protease which accumulates in cells or tissues, producing a recombinant serine protease inhibitor having a protease binding site and a hinge region of a reactive center loop which have modified amino acid sequences so that interaction between the inhibitor and the target protease is altered and contacting cells or tissues with the modified serine protease inhibitor so that activity of the serine protease is modulated. It is preferred that the amino acid sequence of the hinge region of the serine protease inhibitor be modified with amino acids having small and neutral side chains such as alanines and threonines.

In one embodiment the serine protease activity modulated is chymase activity. In this embodiment it is preferred that the serine protease inhibitor be an analogue of human wild type α-1-antichymotrypsin having a modification of amino acid 358 or a modification of amino acids 356–361.

In another embodiment, the serine protease activity modulated is elastase activity. In this embodiment it is preferred that the serine protease inhibitor be an analogue of human wild type α-1-antichymotrypsin having a modification of amino acid 358 or a modification of amino acids 356–361.

The serine protease inhibitors prepared in accordance with the teachings of the present invention can be used in the treatment of diseases related to the abnormal function of proteases or their inhibitors. For example, serine proteases such as elastase, cathepsin G, chymases and tryptases are associated with phagocytosis. Abnormal function of these proteases or their inhibitors is associated with inflammation, emphysema, adult respiratory distress syndrome (ARDS) and rheumatoid arthritis. Serine proteases such as trypsin, chymotrypsin, elastase and enterokinase are involved in digestion. The abnormal function of these proteases or their inhibitors is associated with pancreatitis. Serine proteases such as plasmin and plasminogen activator are associated with fibrinolysis. The abnormal function of these proteases or their inhibitors is associated with tumor invasion. Serine proteases such as Factor IXI, Factor Xa, Factor XIa, Factor XIIa, Factor VIIa, thrombin, activated protein C and plasma kallikrein are involved in blood coagulation. The abnormal function of any of these proteases or their inhibitors is associated with vascular clotting, cerebral infarction, and coronary infarction. Serine proteases such as Factor CIr, Factor CIs, Factor D, Factor B and C3 convertase are involved in complement activation. Abnormal function of these proteases or their inhibitors is associated with rheumatoid arthritis and inflammation. Serine proteases such as tissue kallikrein and post proline cleaving enzymes are involved in hormone generation and degradation. The abnormal function of these proteases or their inhibitors is associated with inflammation. Serine proteases such as plasmin, plasminogen activator and acrosin are involved in ovulation and fertilization. The function of these proteases and their inhibitors is associated with fertility control. ATP-dependent proteases are involved in protein turnover. Abnormalities associated with these proteases and their inhibitors are involved in muscle degradation and fever.

The recombinant serine protease inhibitors of the present invention are administered to a patient in an effective amount in the presence of a pharmaceutically acceptable carrier. By "effective amount" is meant a concentration of recombinant serine protease inhibitor which is capable of modulating an activity of a selected protease. This amount can be routinely determined by one of skill in the art in accordance with the weight, age and clinical condition of the patient. Suitable pharmaceutically acceptable carriers are well known in the art and are described, for example, in Gennaro, Alfonso, ed., *Remington's Pharmaceutical Sciences,* 18th edition, 1990, Mack Publishing Co., Easton, Pa., a standard reference text in this field. Suitable pharmaceutical carriers are selected in accordance with the intended route of administration and standard pharmaceutical practices. Such compositions can be administered by any suitable route including, but not limited to, intravenously, orally, intraperitoneally, intramuscularly, subcutaneously, topically, and by absorption through epithelial or mucocutaneous linings such as nasal, oral, vaginal, rectal, and gastrointestinal. The proportional ratio of active ingredient to pharmaceutical carrier will naturally depend on the chemical nature, solubility, and stability of the recombinant serine protease inhibitor. Compositions prepared in accordance with the disclosed invention may be administered either alone or in combination with other compounds, including but not limited to, other recombinant serine protease inhibitors, antibodies, toxins, and antisense oligonucleotides.

These compositions are also useful in diagnosing and treating patients with deficient amounts of a wild type serine protease inhibitor. Familial α1-Antichymotrypsin (ACT) deficiency, defined as plasma levels of less than 64% normal, has been studied in patients and their relatives with partial deficiency of less than 50% normal. Six out of eight ACT deficient individuals, over 25 years of age, had liver abnormalities, while three out of eight ACT deficient individuals had lung abnormalities. These manifestations varied from severe disease to subtle laboratory abnormalities and appear to be related to an abnormal expression of ACT resulting from a deletion of one or two alleles in the gene for ACT which causes uncontrolled activity of the protease Chtr. Eriksson et al., *Acta Med Scand* 1986, 220, 447. Two defective mutants of human α1-antichymotrypsin (ACT) gene have also been associated with chronic obstructive pulmonary disease (COPD). Poller, W. et al., *Genomics* 1993, 17, 740. A leucine 55-to-proline substitution causing a defective ACT allele was observed in a family with COPD in three subsequent generations. Another mutation, proline 229-to-alanine, was associated with ACT serum deficiency in four patients with a positive family history. In each of these mutations, the physiological manifestations related to the mutation can be alleviated by early diagnosis and treatment of the deficiency. Identification of mutations using well known PCR or RT-PCR techniques and correlation with recombinant serine protease inhibitors of the present invention facilitates diagnosis of such conditions. In addition, the compositions of the invention are useful in treating these deficiencies.

The following nonlimiting examples are provided to further illustrate the present invention.

EXAMPLES

Example 1: Construction and Purification of ACT Analogues

Beginning with the ACT expression vector, pACT, and using standard site-directed mutagenesis, a unique Kpn1 restriction site was created at position corresponding to P10–P9, changing Ala-Ala to Gly-Thr and a Mlu1 restriction site was created at P10'–P11', changing Val to Thr. The association rate constant of variant rACT encoded by this expression vector is $5 \times 10^6$ $M^{-1}S^{-1}$ and has an SI of 1 equivalent to wild type. Cassette variants were then created by removing the Kpn1-Mlu1 fragment and inserting a synthetic double strand oligonucleotide with selected coding sequences. The rACT-P10P10', rACT-P10P5" and rACT-OM mutants were generated in the cassette vector.

The point mutants rACT-T345R, rACT-A347R and rACT-A350R were generated by PCR using standard techniques. A pair of complementary internal primers which encoded a specific mutation were used separately by pairing with their respective external primers for two PCR reactions. The two PCR reactions gave two species which include the mutation site and have complementary ends. Two species mixed at equal molar concentration were used as a mutant template with two external primers for a PCR reaction to amplify the mutant gene. The point mutants rACT-T345R, rACT-A347R and rACT-A350R constructed in this manner were verified by nucleic acid sequencing.

Wild type rACT and mutants were purified by lysing the bacteria in a French press, followed by centrifugation and application of the supernatant to an anion exchange column which was eluted in a salt gradient. The active fraction was applied to a DNA cellulose column and eluted in salt. The pure product showed a single band on SDS-PAGE gel. Mutations prepared by this method are shown in Table 1.

ing a specific activity of 0.02 absorbency units (410 nm)/min/pmol/ml, with Suc-Ala-Ala-Pro-Phe-pNA, SEQ ID

TABLE 1

Mutations to Reactive Center Loop of Antichymotrypsin

| SEQ ID NO | Name | Sequence/Mutation |
|---|---|---|
|  |  | P10    P5    P1 P1'  P5'    P10' |
| 3 | rACT (wild type) | T E A S A A T A V K I T L L S A L V E T R T I V R F N |
| 4 | rACT-L358M | : : : : : : : : : : : : M: : : : : : : : : : : : : : |
| 5 | rACT-L358R | : : : : : : : : : : : : R: : : : : : : : : : : : : : |
| 6 | rACT-L358W | : : : : : : : : : : : : W: : : : : : : : : : : : : : |
| 7 | rACT-V-P3' | : : : : : : : : : : : : : : : V: : : : : : : : : : : |
| 8 | rACT-P3P3' | : : : : : : : : : : I P MS I P : : : : : : : : : : : |
| 9 | rACT-P6-P3 | : : : : : : : L E AI P MS I P : : : : : : : : : : : |
| 10 | rACT-CAS | : : : : G T : : : : : : : : : : : : : : : : T : : : |
| 11 | rACT-CAS-F | : : : : G T : : : : : : F : : : : : : : : : T : : : |
| 12 | rACT-CAS-M | : : : : G T : : : : : : M: : : : : : : : : T : : : |
| 13 | rACT-CAS-P3-P3' | : : : : G T : : : : I P MS I P : : : : : : T : : : |
| 14 | rACT-CAS-P3-P3'/L | : : : : G T : : : : I P L S I P : : : : : : T : : : |
| 15 | rACT-CAS-ElasW | : : : : G T : : : : VI S A E WM: : : : : : T : : : |
| 16 | rACT-CAS-Try | : : : : G T MF L E AI P MS I P P E : : : : T : : : |
| 17 | rACT-P10P5' | : : : : G T MF L E AI P MS I P P E : : : : A : : : |
| 18 | rACT-P10P10' | : : : : G T MF L E AI P MS I P P E VKF NT: : : |
| 19 | rACT-T345R | R: : : : : : : : : : : : : : : : : : : : : : : : : : |
| 20 | rACT-T347R | : : R: : : : : : : : : : : : : : : : : : : : : : : : |
| 21 | rACT-T350R | : : : : : R: : : : : : : : : : : : : : : : : : : : : |
| 22 | rACT-PZM/P3P4'ΔP6'9' | : : : : G T T A VKI I P MS I P P E / / / / T: : : |
| 23 | rACT-PI-P3'R | : : : : : : : : : : I P R S I P : : : : : : : : : : |
| 24 | rACT-Hep Cof II | : : : : : : : : : : MP L S T Q: : : : : : : : : : |
| 25 | rACT-Anti-Thrombin | : : : : : : : : : : A G R S L N: : : : : : : : : : |
| 26 | rACT-Ci Inhibitor | : : : : : : : : : : V A R T L L: : : : : : : : : : |
| 27 | rACT-PAI | : : : : : : : : : : S A R MA P: : : : : : : : : : |
| 28 | rACT-Anti-Plasmin | : : : : : : : : : : M S R MS L: : : : : : : : : : |
| 29 | rACT-Prot C. Inhi | : : : : : : : : : : T F R S A R: : : : : : : : : : |
| 30 | α1P1 (wild type) | T E A AGAMF L E AI P MS I P P E VKF NKP F T |

In this Table, the character ":" denotes the same amino acid as the wild type; and the character "/" denotes a deletion of the amino acid.

Example 2: Inhibition of Human Neutrophil Elastase Activity

Human Neutrophil Elastase concentration was measured, assuming a specific activity of 0.0053 absorbency units (410 nm)/min/pmol/ml, with N-mMeO-Suc-Ala-Ala-Pro-Val-pNA, SEQ ID NO: 1, (final concentration 1.0 mM in 1% $Me_2SBSO$) in 100 mM Hepes, 500 mM NaCl, pH 7.5 at room temperature. The Chtr activity was measured, assuming a specific activity of 0.02 absorbency units (410 nm)/min/pmol/ml, with Suc-Ala-Ala-Pro-Phe-pNA, SEQ ID NO: 2, (final concentration 0.2 mM in 0.2% $Me_2SO$) in 500 mM Tris-HCl, 0.025% Tx-100, pH 8.3 at room temperature. Stoichiometry of inhibition (SI) analyses were carried out in 1 ml containing 100 mM Tris-HCl, pH 8.3, 0.005% (v/v) Triton X-100 and constant amount of Chtr (about 180 μM) and varying the concentration of rACT and mutants. The rate of inhibition by rACT mutants against Chtr were measured at 25° C. under second-order conditions in reaction mixture containing equimolar concentration of Chtr and mutants with inhibitory activity. Data from these experiments is shown in Table 2.

Example 3: Inhibition of Cathepsin G activity

Cathepsin G from human neutrophils was obtained from Athens Research and Technology, Inc. (Athens, GA) and used without further purification. The concentration of cathepsin G was determined under standard assay conditions (0.1M Hepes, 7.5 and 1 mM Suc-AAPF-p-NA at 37° C.) assuming a specific activity of 250 pmole of product per minute. Reactions of cathepsin G (250 nM) with rACT variants were performed at 25° C. in 0.1–0.2 ml of a solution containing one of the following buffers: PBS, pH 7.4; 0.1M Tris-HCl, pH 8.3; 1 M Tris-HCl, pH 7.0; 1.0M NaPi, pH 7.0 or 1 M NaPi, pH 8.3. After incubation with various amounts of inhibitor for 15 to 30 minutes, residual activities were measured spectrophotometrically by dilution (4–8 fold) of a sample aliquot in 0.8 ml standard assay buffer containing 4 mM substrate solution Suc-AAPF-pNA. Rates of substrate hydrolysis were constant over the 2 minute period used to determine residual activities, indicating the cathepsin G:ACT complexes were stable to dilution. Data from these experiments are shown in Table 2.

Example 4: Inhibition of Chymotrypsin Activity

Chymotrypsin (Chtr) activity was measured, assuming a specific activity of 0.02 absorbency units (410 nm)/min/ pmol/ml, with Suc-Ala-Ala-Pro-Phe-pNA, SEQ ID NO: 2, (final concentration 0.2 mM in 0.2% Me$_2$SO) in 500 mM Tris-HCl, 0.025% Tx-100, pH 8.3 at room temperature. Stoichiometry of inhibition (SI) analyses were carried out in a total volume of 1 mL containing 100 mM Tris-HCl, pH 8.3, 0,005% (v/v) Triton X-100 and constant amount of Chtr (about 180 µM) and varying the concentrations of rACT and mutants. The rate of inhibition by rACT mutants against Chtr were measured at 25° C. under second-order conditions in reaction mixture containing equimolar concentration of Chtr and mutants with inhibitory activity. Data from these experiments are shown in Table 2.

Example 5: Inhibition of Chymase Activity

Chymase was purified and its concentration determined as described by Schecter et al., *J. Biol. Chem.* 1993, 268, 23626. Inhibition of chymase by various RACT inhibitors was determined by titration. Chymase (200 nM) was titrated with increasing amounts of rACT variants in reactions containing 1 to 2M NaCl/0.1M Tris-HCL containing 0.01% Triton X-100, pH 8.0, at 25° C. This was accomplished using several reactions of 50 to 100 µl total volume containing an identical amount of chymase and varied amounts of rACT variants. Residual activities after suitable incubation periods were determined by removing an aliquot from each reaction, diluting it to 1 ml with assay buffer containing 1 mM Suc-Ala-Ala-Pro-Phe-pNA (SEQ ID NO: 2) substrate, and monitoring pNA release spectrophotometrically at 410 nm for 3 minutes. Rates of substrate hydrolysis were constant over the 3 minute monitoring period indicating that chymase-ACT complexes were stable to dilution and that residual activities obtained with this method were a reliable measurement of free enzyme in titration reactions. Data was converted to fractional activity and plotted against the $[I]_0/[E]_0$ ratio of each reaction to determine the stoichiometry of inhibition. The rate constant ($k_{obs}/I$) of chymase inhibition by various rACT inhibitors was measured under pseudo-first order conditions in the presence of substrate. Inhibitor concentrations were at least 10 fold higher than the enzyme concentration multiplied by the SI. Observed inhibition rate constants calculated from the data were corrected for the presence of substrate to obtain $K_{obs}/I$ values, Data from these experiments are shown in Table 2.

TABLE 2

Effect of Mutation to Reactive Loop of Antichymotrypsin on Enzyme Inhibition

| SEQ ID NO | Chymotrypsin Inhibition | Cathepsin-G Inhibition | Chymase Inhibition | Human Neutrophil Elastase Inhibition | Thrombin Inhibition | Plasmin Inhibition |
|---|---|---|---|---|---|---|
| 3  | a | a | p | i | p |   |
| 4  | a | a | p | p |   |   |
| 5  | p | p | i |   | a | a |
| 6  |   |   | v |   |   |   |
| 7  | a |   | a |   |   |   |
| 8  | a | a | a | a |   |   |
| 9  | a |   |   | p |   |   |
| 10 | a | a | p | i | p |   |
| 11 | v | v | p |   |   |   |
| 12 | a | a | p | p |   |   |
| 13 | a | a | a | a |   |   |
| 14 | a |   |   | i |   |   |
| 15 | i |   |   | i |   |   |
| 16 | i |   |   |   |   |   |
| 17 | p |   |   | i |   |   |
| 18 | p |   |   | i |   |   |
| 19 | i | i |   | i |   |   |
| 22 | a |   |   | a |   |   |
| 30 |   |   |   | a |   |   |

In Table 2:
"v" means very active, better that any natural serpin inhibitor;
"a" means active;
"p" means partially active; and
"i" means inactive.

What is claimed is:

1. A method of producing a recombinant serine protease inhibitor capable of effectively modulating serine protease activity comprising:
   a) determining a sequence of a selected serine protease inhibitor;
   b) identifying a reactive loop of said serine protease inhibitor, said reactive loop containing a first amino acid sequence of a protease binding site and a second amino acid sequence of a hinge region;
   c) modifying DNA encoding the first amino acid sequence of said protease binding site so that the selectivity of a recombinant serine protease inhibitor for other proteases will be altered;
   d) modifying DNA encoding the second amino acid sequence of said hinge region so that said recombinant serine protease inhibitor is capable of effectively modulating an activity of the protease;
   e) synthesizing said modified recombinant serine protease inhibitor; and
   f) isolating said modified recombinant serine protease inhibitor,
   wherein said modified recombinant serine protease inhibitor is an antichymotrypsin analogue and with the proviso that said antichymotrypsin analoques does not consist of:
   (i) an antichymotrypsin analogue wherein the amino acid corresponding to leucine at position 358 is substituted with arginine or methionine;
   (ii) an antichymotrypsin analogue wherein the amino acids corresponding to alanine-alanine at amino acid positions 349 and 350 of wild type α-1-antichymotrypsin are substituted with glycine-threonine and the amino acids corresponding to valine-arginine at amino acid positions 368 and 369 are substituted with threonine-arginine; or
   (iii) an antichymotrypsin analogue wherein the amino acids corresponding to alanine-alanine at amino acid positions 349 and 350 of wild type α-1-antichymotrypsin are substituted with glycine-threonine, the amino acids correspondinq to valine-arqinine at amino acid positions 368 and 369 are substituted with threonine-arginine and the amino acid at position 358 is substituted with a phenylalanine.

2. The method of claim 1 wherein DNA encoding the second amino acid sequence of said hinge region is modified to encode amino acids having small and neutral side chains.

3. The method of claim 1 wherein the serine protease inhibitor is also capable of binding to DNA.

4. A composition capable of effectively modulating serine protease activity comprising a recombinant antichymotrypsin analogue having a protease binding site and a hinge region of a reactive loop which have modified amino acid sequences with the proviso that said modified amino acid sequences do not consist of:
   (i) modification of the amino acid corresponding to leucine at position 358 being substituted with arginine or methionine;
   (ii) modification of the amino acids corresponding to alanine-alanine at amino acid positions 349 and 350 of wild type α-1-antichymotrypsin being substituted with glycine-threonine and the amino acids corresponding to valine-arginine at amino acid positions 368 and 369 being substituted with threonine-arginine; or
   (iii) modification of the amino acids corresponding to alanine-alanine at amino acid positions 349 and 350 of wild type α-1-antichymotrypsin being substituted with glycine-threonine, the amino acids corresponding to valine-arginine at amino acid positions 368 and 369 being substituted with threonine-arginine and the amino acid at position 358 being substituted with a phenylalanine.

5. The composition of claim 4 wherein said modified amino acid sequence of said hinge region comprises amino acids with small and neutral side chains.

* * * * *

UNITED STATES PATENT AND TRADEMARK OFFICE
CERTIFICATE OF CORRECTION

PATENT NO. : 5,612,194

DATED : March 18, 1997

INVENTOR(S) : Rubin et al.

It is certified that error appears in the above-indentified patent and that said Letters Patent is hereby corrected as shown below:

At col. 2, line 48, please delete "setpins" and insert therefor --serpins--.

At col. 4, line 29, please delete "foundequally" and insert therefor --found equally--.

At col. 5, line 61, please delete "appropriate" and insert therefor --Appropriate--.

At col. 6, line 32, please delete "serlne" and insert therefor --serine--.

At col. 12, line 7, please delete "RACT" and insert therefor --rACT--.

Signed and Sealed this

Sixteenth Day of September, 1997

Attest:

BRUCE LEHMAN

Attesting Officer

Commissioner of Patents and Trademarks